US005760041A

United States Patent [19]
Wissner et al.

[11] Patent Number: 5,760,041
[45] Date of Patent: Jun. 2, 1998

[54] 4-AMINOQUINAZOLINE EGFR INHIBITORS

[75] Inventors: Allan Wissner, Ardsley; Bernard D. Johnson, Stony Point; Middleton B. Floyd, Jr., Suffern; Douglas B. Kitchen, Washingtonville, all of N.Y.

[73] Assignee: American Cyanamid Company, Madison, N.J.

[21] Appl. No.: 785,910

[22] Filed: Jan. 21, 1997

Related U.S. Application Data

[60] Provisional application No. 60/011,128, Feb. 5, 1996.
[51] Int. Cl.$^6$ .................. A61K 31/505; C07D 239/94
[52] U.S. Cl. ................................ 514/259; 544/293
[58] Field of Search ..................... 514/259; 544/293

[56]  References Cited

U.S. PATENT DOCUMENTS

| | | | |
|---|---|---|---|
| 4,343,804 | 8/1982 | Munson et al. | 424/258 |
| 5,475,001 | 12/1995 | Barker | 514/258 |
| 5,480,883 | 1/1996 | Spada et al. | 514/249 |
| 5,580,870 | 12/1996 | Barker et al. | 514/234.5 |
| 5,616,582 | 4/1997 | Barker | 514/234.5 |

FOREIGN PATENT DOCUMENTS

| | | |
|---|---|---|
| 2148324 | 11/1995 | Canada . |
| 520722A1 | 6/1992 | European Pat. Off. . |
| 566226A1 | 1/1993 | European Pat. Off. . |
| 602851A1 | 9/1993 | European Pat. Off. . |
| 635498A1 | 7/1994 | European Pat. Off. . |
| 682027A1 | 4/1995 | European Pat. Off. . |
| WO9515758 | 6/1995 | WIPO . |
| WO9519774 | 7/1995 | WIPO . |
| WO9519970 | 7/1995 | WIPO . |
| WO9521613 | 8/1995 | WIPO . |
| WO9523141 | 8/1995 | WIPO . |
| WO9524190 | 9/1995 | WIPO . |
| WO9609294 | 3/1996 | WIPO . |
| 9738983 | 10/1997 | WIPO . |

OTHER PUBLICATIONS

Pellerano, C., et al., IL Farmaco 45(3):269–284 (1990).
Savini, L..., et al., IL Farmaco 48(6):805–825 (1993).
Dolle, R. E., et al., J. Med. Chem. 37:2627–2629 (1994).
Bridges, A. J., et al., J. Med. Chem. 39:267–276 (1996).
Fry, D.W. et al., Science, 265:1093–1095 (1994).
Ife, R. J. et al., J. Med. Chem. 35:3413–3422 (1992).
Maguire, M. P. et al., J. Med. Chem. 37:2129–2137 (1994).
Marecki, P. E. et al., Journal of Pharmaceutical Science 73:1141–1143 (1984).
Rewcastle, G. W. et al., J. Med. Chem. 38:3482–3487 (1995).
Sarges, R. et al., J. Med. Chem. 36:2828–2830 (1993).

*Primary Examiner*—Matthew V. Grumbling
*Attorney, Agent, or Firm*—Arnold S. Milowsky

[57]  ABSTRACT

This invention provides a compound having the formula

[Structure 1: 4-aminoquinazoline core with substituents R, $R_1$, $R_2$, Y, HN-X]

wherein:

X is phenyl which is optionally substituted;

R and $R_1$ are each, independently, hydrogen, halogen, alkyl, alkoxy, hydroxy, or trifluoromethyl;

$R_2$ is hydrogen, alkyl, alkoxy, hydroxy, trifluoromethyl;

Y is a radical selected from the group consisting of

[Structures showing various Y radicals with $R_3$ substituents]

$R_3$ is independently hydrogen, alkyl, carboxy, carboalkoxy, phenyl, or carboalkyl;

n=2–4;

or a pharmaceutically acceptable salt thereof, with the proviso that each $R_3$ of Y may be the same or different which are useful as antineoplastic agents.

23 Claims, No Drawings

4-AMINOQUINAZOLINE EGFR INHIBITORS

BACKGROUND OF THE INVENTION

This application claims the benefit of U.S. Provisional application Ser. No. 60/011,128 filed Feb. 5, 1996.

This invention relates to certain quinazoline compounds as well as the pharmaceutically acceptable salts thereof. The compounds of the present invention inhibit the action of certain growth factor receptor protein tyrosine kinases (PTK) thereby inhibiting the abnormal growth of certain cell types. The compounds of this invention therefore are anti-cancer agents and are useful for the treatment of cancer in mammals. In addition, this invention relates to the manufacture of said quinazolines, their use for the treatment of cancer, and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., Adv. Cancer Res., 60, 43 (1993) and Parsons, J. T.; Parsons, S. J., Important Advances in Oncology, DeVita V. T. Ed., J.B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., Science, 244, 707 (1989) and Science, 235, 1146 (1987)]. Deregulation of EGF-R kinase has been associated with epidermoid tumors [Reiss, M., et. al., Cancer Res., 51, 6254 (1991)], breast tumors [Macias, A., et. al., Anticancer Res., 7,459 (1987)], and tumors involving other major organs [Gullick, W. J., Brit. Med. Bull., 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., Drugs Future, 17, 119 (1992) and Chang, C. J.; Geahlen, R. L., J. Nat. Prod., 55, 1529 (1992)].

The compounds of this invention are certain 4-anilinoquinazolines. Throughout this patent application, the quinazoline ring system will be numbered as indicated in the formula below:

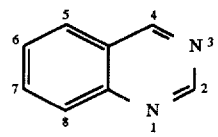

Other 4-anilinoquinazolines which differ both in the nature and placement of the substituents at positions 5–8 compared to the compounds of this invention have been noted to have PTK inhibition activity. It is known from the European Patent Application 520,722 A1 certain 4-anilinoquinazolines which contain at positions 5–8 hydrogen, chloro, trifluoromethyl, or nitro substituents. None of the compounds in the aforementioned application have the unique combination of substituents contained in the compounds of the present invention. In addition, it is noteworthy that although an anti-cancer utility is claimed for the compounds of the aforementioned European Patent Application, no demonstration of an in vivo anti-cancer effect is provided. It is known from the European Patent Application 566,226 A1 certain 4-anilinoquinazolines which optionally contain at positions 5–8 a variety of substituents. None of the compounds in the aforementioned application have the unique combination of substituents contained in the compounds of the present invention. In addition, it is noteworthy that although an anti-cancer utility is claimed for the compounds of the aforementioned European Patent Application, no demonstration of an in vivo anti-cancer effect is provided. The only in vivo activity described in the aforementioned European Patent Application is the inhibition of TGF-alpha stimulated growth of hepatocyte in rats. It is known from the European Patent Application 635,498 A1 certain 4-anilinoquinazolines which optionally have at position 6 a variety of substituents while at position 7 they must have a halogen. None of the compounds in the aforementioned application have the unique combination of substituents contained in the compounds of the present invention. In addition, it is noteworthy that although an anti-cancer utility is claimed for the compounds of the aforementioned European Patent Application, no demonstration of an in vivo anti-cancer effect is provided. The only in vivo activity described in the aforementioned European Patent Application is the inhibition of TGF-alpha stimulated growth of hepatocyte in rats. In addition, certain quinazoline inhibitors that do not have a 4-anilino group are known. It is known from the European Patent Application 602,851 A1 certain quinazolines that do not have an anilino group in the 4 position and which optionally contain at positions 5–8 a variety of substituents. None of the compounds in the aforementioned application have the unique combination of substituents contained in the compounds of the present invention. In addition, it is noteworthy that although an anti-cancer utility is claimed for the compounds of the aforementioned European Patent Application, no demonstration of an in vivo anti-cancer effect is provided. The only in vivo activity described in the aforementioned European Patent Application is the inhibition of TGF-alpha stimulated growth of hepatocyte in rats. It is known from the patent application WO 95/19774 certain heterocycles that are inhibitors of PTKs that have a similar pyrimidine ring to the 4-anilinoquinazoles of the present invention. This aforementioned application makes no mention of 4-anilinoquinazolines nor of the unique combination of substituents contained in the compounds of the present invention. In addition, it is noteworthy that although an anti-cancer utility is claimed for the compounds of the aforementioned application, no demonstration of an in vivo anti-cancer effect is provided. It is known from the patent application WO 95/15758 certain quinazolines which optionally contain at positions 5–7 a variety of substituents. None of the compounds in the aforementioned application have the unique combination of substituents contained in the compounds of the present invention. In addition, it is noteworthy that although an anti-cancer utility is claimed for the compounds of the aforementioned patent application, no demonstration of an in vivo anti-cancer effect is provided.

In addition to the aforementioned patent applications, a number of publications describe 4-anilinoquinazolines: Fry, D. W., et. al., *Science*, 265, 1093 (1994), Rewcastle G. W., et. al., *J. Med. Chem.*, 38, 3482 (1995), and Bridges, A. J., et. al., *J. Med. Chem.*, 39, 267, (1996). None of the compounds described in these publications have the unique combination of substituents contained in the compounds of the present invention. In addition, it is noteworthy that no demonstration of an in vivo anti-cancer effect is described in these reports.

A PTK catalyses the transfer of a phosphate group from a molecule of ATP to a tyrosine residue located on a protein substrate. The inhibitors so far known in the art are usually competitive with either the ATP or the protein substrate of the kinase. Some of these inhibitors, the so-called mixed competitive inhibitors, can be competitive with both ATP and substrate simultaneously; all such competitive inhibitors function as reversible inhibitors. The 4-anilinoquinazolines known in the art are reversible inhibitors that are competitive with ATP [Fry, D. W., et. al., *Science*, 265, 1093 (1994)]. Since the concentration of ATP in a cell is normally very high (millimolar), compounds that are competitive with ATP may lack in vivo activity since it is unlikely that said compounds can reach the concentrations within the cell that are necessary to displace the ATP from its binding site. As demonstrated, the quinazoline inhibitors of this invention have the unique ability of inhibiting these PTKs in an irreversible manner and are therefore non-competitive with ATP or protein substrate. The compounds of this invention can function as irreversible inhibitors by virtue of the fact that they can form covalent bonds to amino acid residues located at the active site of the enzyme. As shown below, this results in an enhanced therapeutic usefulness of the compounds of this invention when compared to the reversible type of inhibitor. In particular, it is shown that it is the unique nature and combination of substituents contained in the compounds of the present invention that lead to the irreversible binding of the inhibitor to the enzyme. These unique properties of the compounds of this invention contribute to their ability to inhibit the growth of human tumors in an in vivo model of cancer.

DESCRIPTION OF THE INVENTION

This invention provides a compound of formula 1:

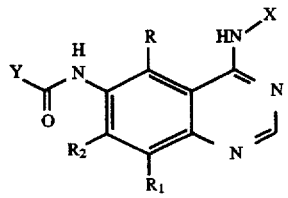

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanaoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

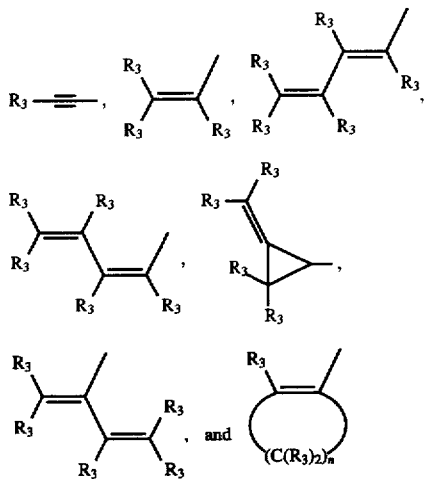

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different.

The pharmaceutically acceptable salts are those derived from such organic and inorganic acids as: acetic, lactic, citric, tararic, succinic, maleic, malonic, gluconic, hydrochloric, hydrobromic, phosphoric, nitric, sulfuric, methanesulfonic, and similarly known acceptable acids.

The alkyl portion of the alkyl, alkoxy, carboalkoxy, carboalkyl, and alkanoylamino substituents include both straight chain as well as branched carbon chains. Carboxy is defined as a —$CO_2H$ radical. Carboalkoxy of 2–7 carbon atoms is defined as a —$CO_2R"$ radical, where R" is an alkyl radical of 1–6 carbon atoms. Carboalkyl is defined as a —COR" radical, where R" is an alkyl radical of 1–6 carbon atoms. When X is substituted, it is preferred that it is mono-, di-, or tri-substituted, with monosubstituted being most preferred. When a compound of this invention contains an assymetric center, this invention covers the individual R and S entantiomers as well as the racemate with respect to such compound.

Of the compounds of this invention, preferred members include those in which R, $R^1$, and $R^2$ are hydrogen; and those in which R, $R^1$, and $R^2$ are hydrogen and X is either unsubstituted or monosubstituted with halogen or alkyl of 1–6 carbon atoms.

The preparation of the compounds of this invention encompassed by Formula 9 is described below in Flowsheet A where R, $R_1$, $R_2$, $R_3$, X, and n are defined and $R_4$ is alkyl of 1–6 carbon atoms (preferably isobutyl). Y' is a radical selected from the group consisting of:

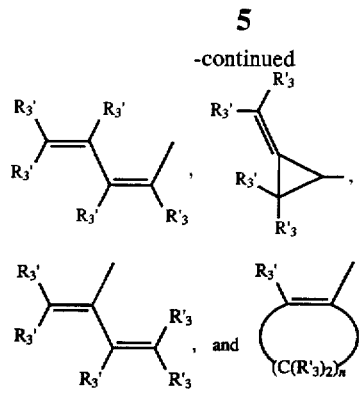

wherein each $R'_3$ is independently alkyl of 1–6 carbon atoms, carboxy, carboalkoxy of 1–6 carbon atoms, phenyl, or carboalkyl of 2–7 carbon atoms. According to the sequence of reaction outlined in flowsheet A, a 5-nitro-anthranilonitrile of Formula 2 is heated at about 100° C. with or without solvent containing an excess of dimethylformamide dimethyl acetal to furnish an amidine of Formula 3. Heating a solution of amidine 3 and the aniline 4 in acetic acid for 1 to 5 hours gives the 6-nitro-4-anilinoquinazolines of Formula 5. Reduction of the nitro group of 5 using a reducing agent such as iron in an acetic acid-alcohol mixture at elevated temperature gives the 6-amino-4-anilinoquinazolines of Formula 6. Acylation of 6 with either an acid chloride of Formula 7 or a mixed anhydride of Formula 8 (which is prepared from the corresponding carboxylic acid) in an inert solvent such as tetrahydrofuran (THF) in the presence of an organic base such as pyridine or triethylamine gives the compounds of this invention represented by Formula 9. In those cases where 7 or 8 have an asymmetric carbon atom, they can be used as the racemate or as the individual R or S entantiomers in which case the compounds of this invention will be in the racemic or R and S optically active forms, respectively. The 5-nitro-anthranilonitriles of Formula 2 needed to prepare the compounds of this invention are either already known to the art or can be prepared by procedures known in the art as detailed in the following references: Baudet, Recl.Trav.Chim.Pays-Bas, 43, 710 (1924); Hartmans, Recl.Trav.Chim.Pays-Bas, 65, 468, 469 (1946); Taylor et al., J.Amer.Chem.Soc., 82, 6058,6063 (1960); Taylor et al., J.Amer.Chem.Soc., 82, 3152,3154 (1960); Deshpande; Seshadri, Indian J.Chem., 11, 538 (1973); Katritzky, Alan R.; Laurenzo, Kathleen S., J.Org.Chem., 51 (1986); Niclas, Hans-Joachim; Bohle, Matthias; Rick, Jens-Detlev; Zeuner, Frank; Zoelch, Lothar, Z.Chem., 25(4), 137–138 (1985).

FLOWSHEET A

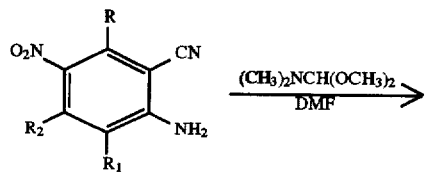

FLOWSHEET A -continued

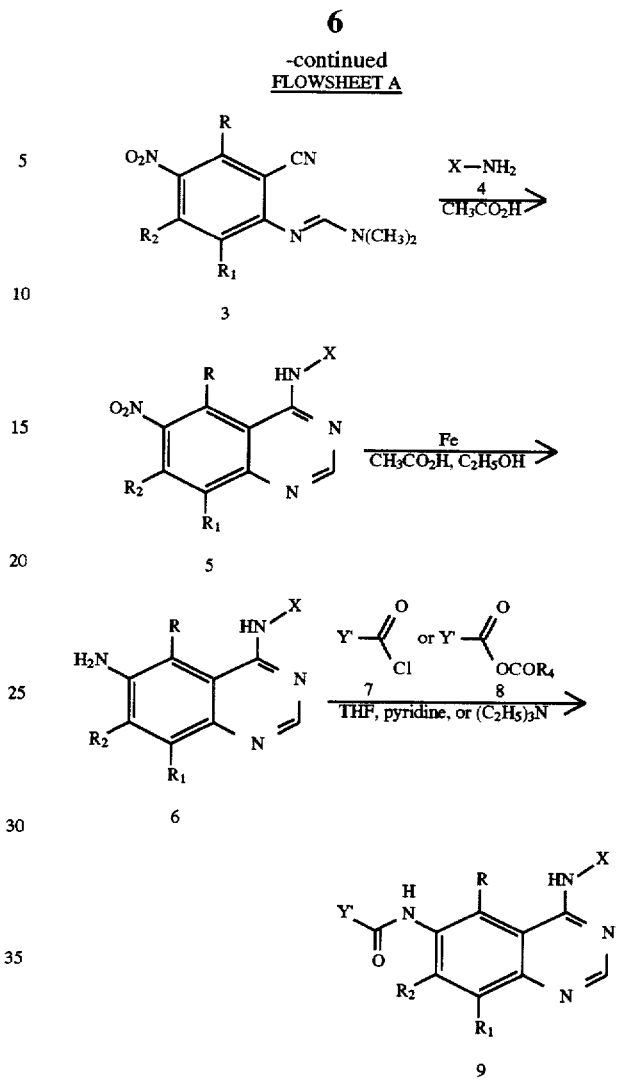

The preparation of the compounds of this invention encompassed by Formula 12 is described below in Flowsheet B wherein R, $R_1$, $R_2$, X, and n are described above. Each $R_5$ is independently hydrogen, phenyl, or alkyl of 1–6 carbon atoms. According to the reaction outlined in Flowsheet B, the 6-amino-4-anilinoquinazolines of Formula 10 (prepared as in Flowsheet A) are acylated with a cyclic anhydride of Formula 11 in an inert solvent such as tetrahydrofuran in the presence of a basic catalyst such as pyridine or triethylamine.

FLOWSHEET B

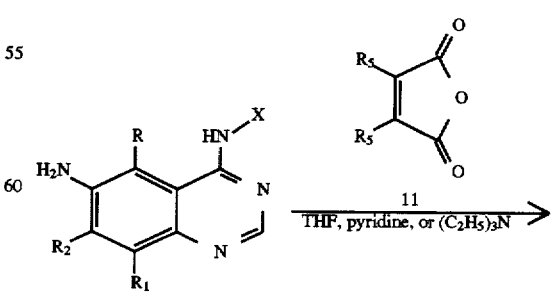

-continued
FLOWSHEET B

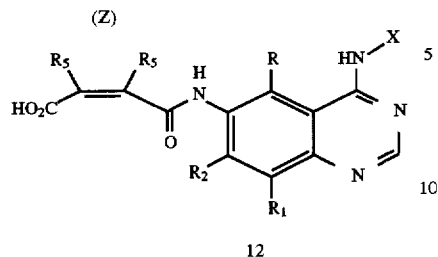

12

Representative compounds of this invention were evaluated in several standard pharmacological test procedures that showed that the compounds of this invention possess significant activity as inhibitors of protein tyrosine kinases, and are antiproliferative agents. Based on the activity shown in the standard pharmacological test procedures, the compounds of this invention are therefore useful as antineoplastic agents. The test procedures used and results obtained are shown below.

The preparation of the compounds of this invention encompassed by Formula 19 is described below in Flowsheet C wherein Y', R$_4$, and X are described above. According to the reactions outlined in Flowsheet C, 4-choro-6-nitroquinazoline, 13, (Morley, J. S. and Simpson, *J. Chem. Soc.*, 360 (1948)) is reduced to 6-amino-4-chloroquinazoline, 14, using a reducing agent such as sodium hydrosulfite in a two phase system consisting of tetrahydrofuran and water in the presence of a small amount of phase transfer catalyst. Acylation of 14 with either an acid chloride of Formula 15 or a mixed anhydride of Formula 16 (which is prepared from the corresponding carboxylic acid) in an inert solvent such as tetrahydrofuran (THF) in the presence of an organic base such as pyridine or N-methyl morpholine gives the compounds of Formula 17. In those cases where 15 or 16 have an asymmetric carbon atom, they can be used as the racemate or as the individual R or S entantiomers in which case the compounds of this invention will be in the racemic or R and S optically active forms, respectively. Heating a compound of Formula 17 with an aniline of Formula 18, in a inert solvent such as isopropanol, gives the compounds of this invention represented by Formula 19.

FLOWSHEET C

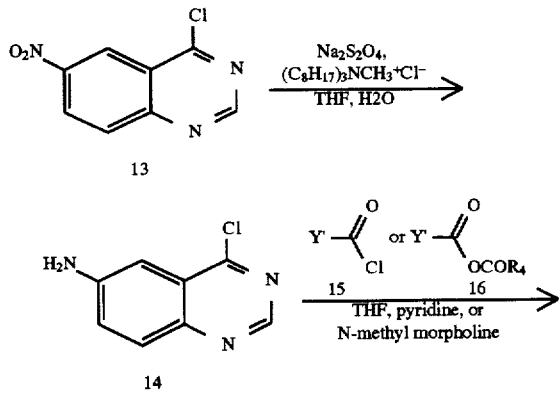

-continued
FLOWSHEET C

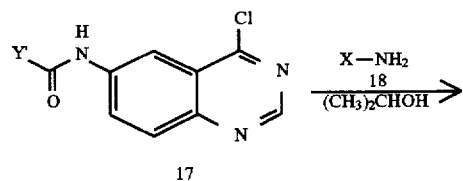

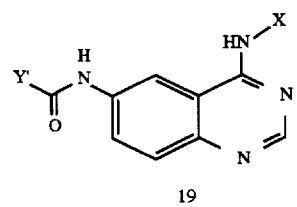

19

The preparation of the compounds of this invention encompassed by Formula 26 is described below in Flowsheet D wherein Y', R$_4$, and X are described above. According to the reactions outlined in Flowsheet D, the nitro group of 20 (prepared as in Flowsheet A) is reduced to the corresponding amino compound 21 using a palladium catalyst and a source of hydrogen which can be hydrogen itself or cyclohexene. Acylation of 21 with either an acid chloride of Formula 22 or a mixed anhydride of Formula 23 (which is prepared from the corresponding carboxylic acid) in an inert solvent such as tetrahydrofuran (THF) in the presence of an organic base such as pyridine or N-methyl morpholine gives the compounds of Formula 24. In those cases where 22 or 23 have an asymmetric carbon atom, they can be used as the racemate or as the individual R or S entantiomers in which case the compounds of this invention will be in the racemic or R and S optically active forms, respectively. Heating a compound of Formula 24 with an aniline of Formula 25, in a inert solvent such as acetic acid gives the compounds of this invention represented by Formula 26.

FLOWSHEET D

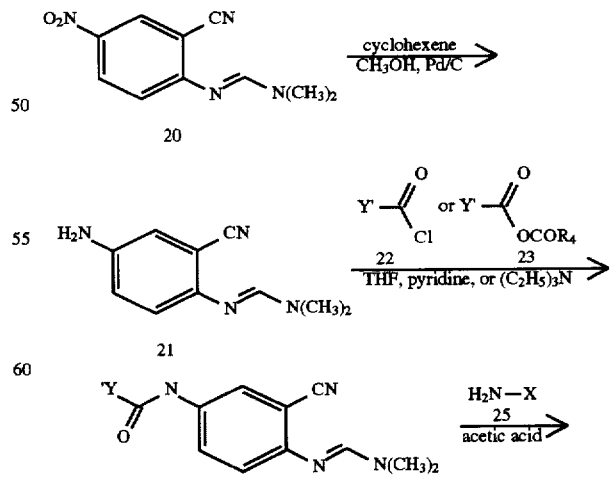

-continued
FLOWSHEET D

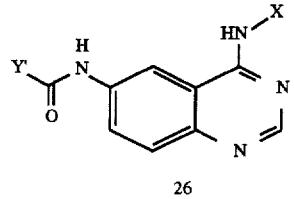

26

Inhibition of Epidermal Growth Factor Receptor Kinase (EGF-R)

Test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-glu-asp-ala-glu-tyr-ala-ala-arg-gly. The enzyme was obtained as a membrane extract of A431 cells (American Type Culture Collection, Rockville, Md.). A431 cells were grown in T175 flasks to 80% confluency. The cells were washed twice with phosphate buffered saline (PBS) without $Ca^{2+}$. Flasks were rotated for 1.5 hours in 20 ml PBS with 1.0 mM ethylenediaminetetraacetic acid (EDTA) at room temperature and centrifuged at 600 g for 10 minutes. The cells were solubilized in 1 ml per $5 \times 10^6$ cells of cold lysis buffer {10 mM 4-(2-hydroxyethyl)-1-piperazineethanesulfonic acid (HEPES), pH 7.6, 10 mM NaCl, 2 mM EDTA, 1 mM phenylmethylsulfonyl-fluoride (PMSF), 10 mg/ml aprotinin, 10 mg/ml leupeptin, 0.1 mM sodium orthovanadate} in a Dounce homogenizer with 10 strokes on ice. The lysate was centrifuged at 600 g for 10 minutes first to clear cell debris and the supernatant further centrifuged at 100,000 g. for 30 min at 4° C. The membrane pellet was suspended in 1.5 ml HNG buffer (50 mM HEPES, pH 7.6, 125 mM NaCl, 10% glycerol). The membrane extract was divided into aliquots, immediately frozen in liquid nitrogen and stored at −70° C.

Test compounds were made into 10 mg/ml stock solutions in 100% dimethylsulfoxide (DMSO). Prior to experiment, stock solutions were diluted to 500 mM with buffer (30 mM Hepes pH 7.4) and then serially diluted to the desired concentration.

An aliquot of the A431 membrane extract (10 mg/ml) was diluted in 30 mM HEPES (pH 7.4) to give a protein concentration of 50 ug/ml. To 4 μl of enzyme preparation, EGF (1 μl at 12 μg/ml) was added and incubated for 10 min on ice followed by 4 μl of the test compound or buffer; this mix was incubated on ice for 30 min. To this was added the $^{33}$P-ATP (10 mCi/ml) diluted 1:10 in assay buffer along with the substrate peptide at a concentration of 0.5 mM (control reactions get no test compound) and the reaction was allowed to proceed for 30 min at 30° C. The reaction was stopped with 10% TCA and left on ice for at least 10 min after which tubes were microcentrifuged at full speed for 15 min. The a portion of the supernatants were spotted on P81 phosphocellulose discs and washed twice in 1% acetic acid then water for 5 min each followed by scintillation counting. The inhibition data for representative compounds of the invention are shown below in TABLE 1. The $IC_{50}$ is the concentration of test compound needed to reduce the total amount of phosphorylated substrate by 50%. The % inhibition of the test compound was determined for at least three different concentrations and the $IC_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabled ATP (g-$^{33}$P) incorporated onto the RR-SRC peptide substrate by the enzyme after 30 minutes at 30° C. in the presence of test compound as measured by liquid scintillation counting. CPM(control) is in units of counts per minute and was a number expressing the amount of radiolabled ATP (g-$^{33}$P) incorporated onto the RR-SRC peptide substrate by the enzyme after 30 minutes at 30° C. in the absence of test compound as measured by liquid scintillation counting. The CPM values were corrected for the background counts produced by ATP in the absence of the enzymatic reaction. The $IC_{50}$ values reported in TABLE 1 are averages of the number of tests conducted.

TABLE 1

Inhibition of Epidermal Growth Factor Receptor Kinase

| Compound | $IC_{50}$ (μM) | Number of Tests |
|---|---|---|
| Example 4 | 0.012 | 5 |
| Example 5 | 0.198 | 4 |
| Example 6 | 0.5 | 1 |
| Example 7 | 0.05 | 1 |
| Example 8 | 0.04 | 2 |
| Example 9 | 0.002 | 20 |
| Example 10 | 0.11 | 2 |
| Example 11 | 0.056 | 4 |
| Example 13 | $10^{-7}$ | 1 |
| Example 14 | 1.0 | 1 |

Determination of Covalent Binding of Test Compound to Epidermal Growth Factor Receptor Kinase An aliquot of the A431 enzyme extract (prepared as described above) was diluted to 50–100 μg/ml with 30 mM Hepes buffer at pH 7.4 containing EGF at 12 μg/ml concentration so that under standard test conditions approximately 2% reaction will take place and the final EGF concentration is 2.4 μg/ml (as in the standard assay describe above). This mixture was incubated at least 10 minutes at 4° C. before use. This enzyme preparation was used for the following dialysis test procedures.

To 60 μl of the enzyme preparation was added 48 μl of test compound dissolved in 5% dimethylsulfoxide (DMSO) (or just 48 μl 5% DMSO for the control). Test compound concentrations were chosen to be 20–100 fold above the IC50 value to ensure ideally 80–90% inhibition. The enzyme-inhibitor solution was incubated for 45–60 minutes at 4° C. For the undialyzed control test procedures, a 9 μl aliquot of the enzyme-inhibitor solution was evaluated under standard protocols as described above. For dialysis test procedures, a 60 μl aliquot of the enzyme-inhibitor solution was placed in a well of a Pierce Microdialyzer System 100 and dialyzed at 4° C. versus 30 mM Hepes containing 1.25 μg/ml EGF for 24 hours with two changes of buffer (minimum 3 hours dialysis before each change). The 8000 molecular weight cutoff membranes were used. A 9 μl (at least duplicates) aliquot of the dialyzed solution was evaluated for activity by the standard protocol as described above. Enzyme without added test compound retains 50–90% of its initial activity after dialysis. Dialyzed solutions of test compound without added enzyme are also evaluated to ensure the compounds are dialyzable.

If the enzymatic activity is not recovered after dialysis, then it is determined that the test compounds is binding covalently (irreversible inhibition). If the enzymatic activity is largely recovered after dialysis, then it is determined that the test compound is binding non-covalently (reversible inhibition). Determinations of covalent binding can be expressed as the % Recovered Activity which is calculated using the following formula which utilize the % inhibition before and after dialysis:

% Recovered Activity=[(% inhibition{pre dialysis}-% inhibition{post dialysis})/% inhibition{pre dialysis}]×100

A value for the % Recovered Activity close to 100% indicates non-covalent binding (reversible inhibition). A value for the % Recovered Activity much below 100% indicates covalent binding (irreversible inhibition). The results obtained for the determinations of covalent binding to EGF-R kinase for representative compounds of this invention are provided below in TABLE 2. For comparison purposes, TABLE 2 also provides binding data for N-(3-bromophenyl)-6,7-dimethoxy-4-quinazolinamine. This quinazoline inhibitor has been identified as a potent inhibitor of EGF-R kinase [Fry, D. W., et. al., *Science*, 265, 1093 (1994); Rewcastle G. W., et. al., *J. Med. Chem.*, 38, 3482 (1995), and Bridges, A. J., et. al., *J. Med. Chem.*, 39, 267, (1996)] and is encompassed in the European Patent Application 566,226 A1. The results of multiple independent evaluations for each compound evaluated are provided in TABLE 2:

TABLE 2

Determination of Covalent Binding to Epidermal Growth Factor Receptor Kinase

| Compound | % Recovered | Activity | Determination |
|---|---|---|---|
| Example 4 | 20 | 11 | 17 covalent (irreversible binding) |
| Example 9 | 9 | 4 | covalent (irreversible binding) |
| N-(3-bromophenyl)-6,7-dimethoxy-4-quinazolinamine | 102 | 70 | 107 non-covalent (reversible binding) |

The results in TABLE 2 show that the compounds of this invention inhibit EGF-R kinase in an irreversible manner by forming a covalent linkage to an amino acid residue located on the enzyme. In this respect, they are distinctly different from the usual 4-anilinoquinazolines such as N-(3-bromophenyl)-6,7-dimethoxy-4-quinazolinamine which binds in a reversible manner. As will be delineated below, this difference in binding abilities between the compounds of this invention and the usual quinazolines inhibitors of the prior art, leads to significantly improved biological activity and therefore greater therapeutic usefulness.

Inhibition of Cell Growth as Measured by the Incorporation of [$^3$H]-Thymidine Representative compounds of this invention were evaluated for their ability to inhibit the growth of the cell lines described below in vitro. The inhibition is quantitated by measuring the decrease in the incorporation of radio-labeled thymidine when the cells are grown in the presence of the inhibitor. A431 and SKBR3 cell lines are obtained from American Type Culture Collection, Rockville, Md. Neu-3T3 cells are obtained by transfecting NIH 3T3 mouse fibroblasts with an activated rat Neu oncogene. NHEK cells are obtained from Clonetics (San Diego, Calif.). Cells were routinely grown in a humidified incubator in 5% $CO_2$ in air. These cell lines are dependent on growth factors which are ligands to the receptor tyrosine kinases that are the targets of the compounds of this invention, and have the following characteristics:

A431: human epidermoid carcinoma cells overexpressing EGFR

Neu-3T3: NIH 3T3 cells transfected with activated Neu oncogene

NHEK: EGF dependent normal human epidermal keratinocytes

SKBR3: Human breast cancer cells overexpressing ErbB2 gene

The cell lines were grown in appropriate media as described below:

A431: Dulbecco's Modified Eagles Media, high glucose, BRL/Gibco (10% Fetal Bovine Serum (FBS), Glutamine, Penicillin-Streptomycin) Dulbecco, R., Freeman, G. *Virology* 8, 396 (1959).

Neu-3T3: Dulbeccos Modified Eagles Media, high glucose (10% Fetal Bovine Serum, Glutamine, Penicillin-Streptomycin)

SKBR3: Roswell Park Memorial Institute 1640 W/GLU (10% FBS, GLU, PS) Moore, G. E., Gerner, R. E. and Franklin, H. A. A.M.A., 199, 516 (1967).

NHEK: Keratinocyte Growth Media, Clonetics Boyce, S. T. and Ham, R. G. In Vitro 17, 239 (Abstract No. 159) (1981)

Cells were seeded at 10,000 cells/well in 96 well plates in complete media and allowed to grow to log phase. At this stage the complete media was replaced with media containing 0.5% FBS (for cells growing in 10% FBS) or media lacking epidermal growth factor (EGF) (for cells growing in serum free media). After overnight incubation in low serum (or EGF lacking) media, the compounds to be evaluated were added and cells remained in the presence of compounds for 48 to 72 hours. Media with test compound was then removed and complete media was added back. The cells were allowed to grow for 18 hours. This is followed by incubation in [$^3$H]thymidine (1mCi/ml in serum/EGF media) for 4 hours. Cells were lysed in 0.5M NaOH for at least 30 min at 37° C. and radioactivity analyzed.

The cell growth inhibition data is provided below in TABLE 3. The $IC_{50}$ is the concentration of test compound needed to reduce the amount of [$^3$H]thymidine incorporation by 50%. The % inhibition of the compound evaluated was determined for at least three different concentrations and the $IC_{50}$ value evaluated from the dose response curve. The % inhibition is evaluated with the following formula:

% inhibition=100-[CPM(drug)/CPM(control)]×100 where CPM(drug) is in units of counts per minute and is a number expressing the amount of [$^3$H]thymidine incorporated into the DNA when cells are grown in the presence of test compound as measured by liquid scintillation counting. CPM(control) is in units of counts per minute and is a number expressing the amount of [$^3$H]thymidine incorporated onto the DNA when cells are grown in the absence of test compound as measured by liquid scintillation counting.

TABLE 3

Inhibition of Cell Growth as Measured by the Incorporation of [$^3$H]-Thymidine ($IC_{50}$)

| Compound | A431 (μM) | SKBR3 (μM) | NHEK (μM) | NEU-3T3 (μM) |
|---|---|---|---|---|
| Example 4 | 0.07 | >50 | 0.17 | >50 |
| Example 5 | 0.825 | 0.30 | 0.17 | 10 |
| Example 6 | 27 | >50 | 4.5 | >50 |
| Example 7 | 0.45 | 5.5 | 0.45 | 7.5 |

TABLE 3-continued

Inhibition of Cell Growth as Measured by the Incorporation of [³H]-Thymidine (IC₅₀)

| Compound | A431 (μM) | SKBR3 (μM) | NHEK (μM) | NEU-3T3 (μM) |
|---|---|---|---|---|
| Example 8 | 0.22 | 7 | 0.5 | 0.3 |
| Example 9 | 0.011 | 1.057 | 0.002 | 0.002 |
| Example 10 | 60 | >50 | >50 | 15 |
| Example 11 | 0.8 | 4 | 0.85 | 0.4 |

In Vivo Inhibition of the Growth of Human Epidermoid Tumors (A431)

BALB/c nu/nu female mice (Charles River, Wilmington, Mass.) were used in the in vivo standard pharmacological test procedures. Human epidermoid carcinoma cells A-431 (American Type Culture Collection, Rockville, Md. # CRL-155) were grown in vitro as described above. A unit of 5×10⁶ cells were injected SC into mice. When tumors attained a mass of between 100 and 150 mg, the mice were randomized into treatment groups (day zero). Mice were treated IP once a day either on days 1, 5, and 9 or on days 1 through 10 post staging with doses of either 80, 40 or 20 mg/kg/dose of the compound to be evaluated in 0.2% Klucel. Control animals received no drug. Tumor mass was determined every 7 days [(length×width²)/2] for 28 days post staging. Relative tumor growth (Mean tumor mass on day 7, 14, 21, and 28 divided by the mean tumor mass on day zero) is determined for each treatment group. The % T/C (Tumor/Control) is determined by dividing the relative tumor growth of the treated group by the relative tumor growth of the placebo group and multiplying by 100. A compound is considered to be active if the % T/C is found to be ≦42%.

The inhibition results obtained for the compound of Example 9 are provided below in TABLE 4.

TABLE 4

In Vivo Inhibition of the Growth of Human Epidermoid Tumors (A431) in Mice by the Compound of Example 9

| Dose (mg/kg/dose)ᵃ IP | RTGᵇ Day 7 | % T/Cᶜ | RTGᵇ Day 16 | % T/Cᶜ | RTGᵇ Day 21 | % T/Cᶜ | RTGᵇ Day 28 | % T/Cᶜ | S/Tᵈ |
|---|---|---|---|---|---|---|---|---|---|
| *Control | 3.68 | | 7.91 | | 11.41 | | 15.04 | | 10/10 |
| *80 | 0.71 | 18 | 0.91 | 11 | 1.07 | 9 | 1.36 | 9 | 5/5 |
| *40 | 1.48 | 40 | 2.23 | 28 | 3.05 | 27 | 4.04 | 27 | 5/5 |
| *20 | 1.72 | 47 | 2.69 | 34 | 4.33 | 38 | 6.18 | 41 | 5/5 |
| **20 | 0.75 | 20 | 1.01 | 13 | 1.25 | 11 | 2.53 | 17 | 5/5 |

ᵃDrugs administered IP on days 1, 5, 9 * or on days 1 through 10 **.

ᵇRelative Tumor Growth = $\frac{\text{Mean Tumor Mass on Day 7, 14, 21, 28}}{\text{Mean Tumor Mass on Day 0}}$ ᶜ% T/C = $\frac{\text{Relative Tumor Growth of Treated Group}}{\text{Relative Tumor Growth of Placebo Group}} \times 100$ ᵈS/T = No. Survivors/No. Treated on Day +28 post tumor staging.

The ability of the compound of Example 9 and N-(3-bromophenyl)-6,7-dimethoxy-4-quinazolinamine to inhibit the growth of human epidermoid tumors (A431) in vivo are compared below in TABLE 5N-(3-Bromophenyl)-6,7-dimethoxy-4-quinazolinamine was chosen as the comparison compound since this quinazoline inhibitor has been identified as a potent inhibitor of EGF-R kinase [Fry, D. W., et. al., *Science*, 265, 1093 (1994); Rewcastle G. W., et. al., *J. Med. Chem.*, 38, 3482 (1995); Bridges, A. J., et. al., *J. Med. Chem.*, 39, 267 (1996)] and is encompassed in the European Patent Application 566,226 A1.

TABLE 5

A Comparison of the In Vivo Inhibition by the Compound of Example 9 and N-(3-Bromophenyl)-6,7-dimethoxy-4-quinazolinamine of the Growth of Human Epidermoid Tumors (A431) in mice. Dose 20 mg/kg/dose IP

| Compound | RTGᵇ Day 7 | % T/Cᶜ | RTGᵇ Day 14 | % T/Cᶜ | RTGᵇ Day 21 | % T/Cᶜ | RTGᵇ Day 28 | % T/Cᶜ | S/Tᵈ |
|---|---|---|---|---|---|---|---|---|---|
| *Control | 3.18 | | 5.65 | | 7.79 | | 10.3 | | 10/10 |
| Example 9 | 1.11 | 35 | 1.26 | 22 | 1.51 | 19 | 2.55 | 22 | 14/15 |

TABLE 5-continued

A Comparison of the In Vivo Inhibition by the Compound of Example 9 and N-(3-Bromophenyl)-6,7-dimethoxy-4-quinazolinamine of the Growth of Human Epidermoid Tumors (A431) in mice. Dose 20 mg/kg/dose IP

| Compound | RTG[b] Day 7 | % T/C[c] | RTG[b] Day 14 | % T/C[c] | RTG[b] Day 21 | % T/C[c] | RTG[b] Day 28 | % T/C[c] | S/T[d] |
|---|---|---|---|---|---|---|---|---|---|
| N-(3-Bromophenyl)-6,7-dimethoxy-4-quinazolinamine | 3.03 | 95 | 6.58 | 116 | 10.5 | 128 | 14.47 | 140 | 15/15 |

[a]Drugs administered IP on days 1 through 15.

[b]Relative Tumor Growth = $\frac{\text{Mean Tumor Mass on Day 7, 14, 21, 28}}{\text{Mean Tumor Mass on Day 0}}$

[c]% T/C = $\frac{\text{Relative Tumor Growth of Treated Group}}{\text{Relative Tumor Growth of Placebo Group}} \times 100$

[d]S/T = No. Survivors/No. Treated on Day +28 post tumor staging.

As shown in TABLES 4–5, the compounds of this invention inhibit the growth of human tumors in mammals and are therefore useful as antineoplastic agents. In this respect, they are distinctly different from the usual 4-anilinoquinazolines such as N-(3-bromophenyl)-6,7-dimethoxy-4-quinazolinamine which is devoid of antineoplastic activity.

The ability of the compound of Example 9 to inhibit the growth of human epidermoid tumors (A431) in vivo was compared with two structurally similar compounds N-[4-[(3-methylphenyl)amino]-6-quinazolinyl]-7-fluoro-2-propenamide (referred to as Comparator A) and N-[4-[(3-bromophenyl)amino]-6-quinazolinyl]-butanamide (referred to as Comparator B) which are covered by European Patent Applications 635,498A1 and 566,226 A1, respectfully. The results of these comparisons are shown in Tables 6 and 7.

TABLE 6

A Comparison of the In Vivo Inhibition by the Compound of Example 9 and N-[4-[(3-Methylphenyl)amino]-6-quinazolinyl]-7-fluoro-2-propenamide (Comparator A) of the Growth of Human Epidermoid Tumors (A431) in mice.

| Compound[a] | RTG[b] Day 7 | % T/C[c] | RTG[b] Day 14 | % T/C[c] | RTG[b] Day 21 | % T/C[c] | S/T[d] |
|---|---|---|---|---|---|---|---|
| Control | 5.52 | | 11.63 | | 7.79 | | 10/10 |
| Example 9 (80 mg/kg) | 1.25 | 18* | 2.50 | 21* | 3.77 | 24* | 10/10 |
| Comparator A (80 mg/kg) | 3.39 | 61 | 5.60 | 48 | 7.68 | 48 | 10/10 |
| Example 9 (20 mg/kg) | 0.79 | 14* | 1.39 | 12* | 2.55 | 16* | 10/10 |
| Comparator A (20 mg/kg) | 4.82 | 87 | 7.36 | 63 | 8.75 | 56 | 9/10 |

[a]Drugs administered IP. Control and the 80 mg/kg doses were administered on days 1, 5, and 9; 20 mg/kg doses were administered on days 1 through 10.

[b]Relative Tumor Growth = $\frac{\text{Mean Tumor Mass on Day 7, 14, 21}}{\text{Mean Tumor Mass on Day 0}}$

[c]% T/C = $\frac{\text{Relative Tumor Growth of Treated Group}}{\text{Relative Tumor Growth of Placebo Group}} \times 100$

[d]S/T = No. Survivors/No. Treated on Day +21 post tumor staging.

*Indicates statistical significance of p < 0.01.

TABLE 7

A Comparison of the In Vivo Inhibition by the Compound of Example 9 and N-[4-[(3-Bromophenyl)amino]-6-quinazolinyl]-butanamide (Comparator B) of the Growth of Human Epidermoid Tumors (A431) in mice.

| Compound[a] | RTG[b] Day 7 | % T/C[c] | RTG[b] Day 14 | % T/C[c] | RTG[b] Day 21 | % T/C[c] | RTG[b] Day 28 | % T/C[c] | S/T[d] |
|---|---|---|---|---|---|---|---|---|---|
| Control | 3.56 | | 5.55 | | 5.85 | | 7.63 | | 10/10 |
| Example 9 (80 mg/kg) | 0.89 | 25* | 1.50 | 27* | 2.44 | 42* | 3.45 | 45* | 5/5 |
| Comparator B (80 mg/kg) | 3.37 | 95 | 5.43 | 98 | 6.21 | 106 | 10.26 | 142 | 5/5 |

TABLE 7-continued

A Comparison of the In Vivo Inhibition by the Compound of Example 9 and N-[4-[(3-Bromophenyl)amino]-6-quinazolinyl]-butanamide (Comparator B) of the Growth of Human Epidermoid Tumors (A431) in mice.

| Compound[a] | $RTG^b$ Day 7 | % T/C[c] | $RTG^b$ Day 14 | % T/C[c] | $RTG^b$ Day 21 | % T/C[c] | $RTG^b$ Day 28 | % T/C[c] | S/T[d] |
|---|---|---|---|---|---|---|---|---|---|
| Comparator B (20 mg/kg) | 2.90 | 81 | 4.19 | 75 | 5.62 | 96 | 8.04 | 105 | 5/5 |

[a]Drugs administered IP. Control and the 80 mg/kg doses were administered on days 1, 5, and 9; 20 mg/kg dose was administered on days 1 through 10.

[b]Relative Tumor Growth = $\dfrac{\text{Mean Tumor Mass on Day 7, 14, 21, 28}}{\text{Mean Tumor Mass on Day 0}}$

[c]% T/C = $\dfrac{\text{Relative Tumor Growth of Treated Group}}{\text{Relative Tumor Growth of Placebo Group}} \times 100$

[d]S/T = No. Survivors/No. Treated on Day +28 post tumor staging.

*Indicates statistical significance of $p < 0.01$.

The results obtained in Tables 6 and 7 show that the compound of Example 9, a representative compound of this invention, significantly ($p<0.01$) inhibited human epidermoid tumor growth in vivo. The structurally closest compounds of European Patent Applications 635,488A1 (Comparator A) and 566,226 A1(Comparator B) were substantially less active than the compound of Example 9, and both failed to significantly reduce tumor growth at both doses tested.

Based on the results obtained for representative compounds of this invention, the compounds of this invention are particularly useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, and antiestrogens such as tamoxifen.

The preparation of representative examples of the compounds of this invention is described below.

EXAMPLE 1

N'-(2-Cyano-4-nitrophenyl)-N,N-dimethylformamidine

A 40.8 g portion of 5-nitro-anthranilonitrile and 40 ml of N, N-dimethylformamide dimethyl acetal were heated on a steam bath for 2 hours. The solvents were removed at reduced pressure and the residue was taken up in methylene chloride. After passing this solution through Magnesol the solvent was removed. After washing with ether 50.8 g of N'-(2-cyano-4-nitrophenyl)-N,N-dimethylformamidine was obtained.

EXAMPLE 2

N-(3-Bromophenyl)-6-nitro-4-quinazolinamine

A solution of 23.74 ml of 3-bromo aniline and 40.5 g N'-(2-cyano-4-nitrophenyl)-N,N-dimethylformamidine in 100 ml of glacial acetic acid was stirred and heated in an oil bath at 148° C. for 1.5 hours. On cooling, filtration of the resulting solid gives a quantitative yield of N-(3-bromophenyl)-6-nitro-4-quinazolinamine: mp=267°–270° C.; mass spectrum (m/e): 345.

EXAMPLE 3

N-(3-Bromophenyl)-4,6-quinazolindiamine

A mixture of 34.5 g of N-(3-bromophenyl)-6-nitro-4-quinazolinamine and 16.8 g of iron powder in 150 ml of ethanol and 150 ml of glacial acetic acid was heated in an oil bath at 120° C. for 2 hours. After filtration of the solid, solid sodium carbonate was added to the filtrate giving a solid. This was filtered, and the solid was extracted with methanol. The extracts were treated with charcoal and evaporated to a solid. After washing the solid with ether 27.5 g of N-(3-bromophenyl)-4,6-quinazolindiamine was obtained: mass spectrum (m/e): 315.

EXAMPLE 4

4-[[4-[(3-Bromophenyl)amino]-6-quinazolinyl] amino]-4-oxo-(Z)-2-butenoic acid

A 15 ml portion of pyridine was added to 1.6 g of N-(3-bromophenyl)-4,6-quinazolindiamine and 0.6 g of maleic anhydride. After stirring overnight, the solvents were removed on the rotary evaporator. The solid was taken up in about 400 ml of hot ethanol and the insoluble material filtered to give 0.33 g of 4-[[4-[(3-Bromophenyl)amino]-6-quinazolinyl]amino]-4-oxo-(Z)-2-butenoic acid: mass spectrum (m/e): M+H 413, 415.

EXAMPLE 5

4-[[4-[(3-Bromophenyl)amino]-6-quinazolinyl] amino]-4oxo-(E)-2-butenoic acid, ethyl ester A solution of N-(3-bromophenyl)-4,6-quinazolindiamine in 15 ml of pyridine was cooled in an ice bath and a solution of 1.22 g of ethyl fumaryl chloride in 10 ml of methylene chloride was added dropwise. After stirring for 1.5 hours, the reaction was allowed to come to room temperature. The solvents were removed at reduced pressure and the residue was treated with water. The red solid was filtered and extracted into hot acetone. After filtration of the insoluble material, the filtrate was concentrated to give 0.45 g of 4-[[4-[(3-Bromophenyl)amino]-6-quinazolinyl]amino]-4-oxo-(E)-2-butenoic acid, ethyl ester: mp=259°–263° C., mass spectrum (m/e): M+H 441, 443.

EXAMPLE 6

N-[4-[(3-Bromophenyl)amino]-6-quinazolinyl]-3-methyl-2-butenamide

A solution of 1.58 g of N-(3-bromophenyl)-4,6-quinazolindiamine in 15 ml of pyridine was cooled in an ice bath and a solution of 0.67 ml of 3,3-dimethylacryloyl chloride in 7 ml of ether was added dropwise. After stirring and cooling for 2 hours, the solvents were removed at reduced pressure. The residue was treated with water and the resulting solid was recrystallized from methyl cellusolve to give 0.97 g of N-[4-[(3-bromophenyl)amino]-6-quinazolinyl]-3-methyl-2-butenamide: mp=300°–301° C., mass spectrum (m/e): 396, 398.

EXAMPLE 7

N-[4-[(3-Bromophenyl)amino]-6-guinazolinyl]-(E)-2-butenamide

A solution of 1.6 g of N-(3-bromophenyl)-4,6-quinazolindiamine in 15 ml of pyridine was cooled in an ice bath and a solution of 0.57 ml of trans-crotonoyl chloride in 6 ml of ether was added dropwise. After stirring and cooling for 2 hours, the solvents were removed at reduced pressure. The residue was treated with water and the resulting solid recrystallized from n-butanol to give 0.69 g of N-[4-[(3-bromophenyl)amino]-6-quinazolinyl]-(E)-2-butenamide: mp=153°–160° C., mass spectrum (m/e): M+H 383, 385.

EXAMPLE 8

N-[4-[(3-Bromophenyl)amino]-6-quinazolinyl]-2-methyl-2-propenamide

A solution of 1.6 g of N-(3-bromophenyl)-4,6-quinazolindiamine in 15 ml of pyridine was cooled in an ice bath and a solution of 0.59 ml of methacryoyl chloride in 6 ml of ether was added dropwise. After stirring and cooling for 2 hours, the solvents were removed at reduced pressure. The residue was treated with water and the resulting solid was taken up in n-butanol (warming). Addition of ether to the cooled solution gives 0.44 g of N-[4-[(3-bromophenyl)amino]-6-quinazolinyl]-2-methyl-2-propenamide: mp=40°–245° C., mass spectrum (m/e): M+H 383, 385.

EXAMPLE 9

N-[4-[(3-Bromophenyl)amino]-6-quinazolinyl]-2-butynamide

A solution of 0.50 g of 2-butynoic acid in 10 ml of tetrahydrofuran was cooled in an ice bath. A 0.79 ml portion of isobutyl chloroformate followed by a 0.66 ml portion of N-methyl morpholine were added. After about 1 minute a solution of 1.6 g of N-(3-bromophenyl)-4,6-quinazolindiamine in 10 ml of pyridine was added. The reaction was allowed to come to room temperature and stir overnight. The solvents were removed at reduced pressure and the solid was recrystallized from n-butanol to give 1.07 g of N-[4-[(3-bromophenyl)amino]-6-quinazolinyl]-2-butynamide: mass spectrum (m/e): 381, 383.

EXAMPLE 10

4-[[4-[(3-Bromophenyl)amino]-6-quinazolinyl]amino]-4-oxo-(E)-2-butenoic acid

A 2.5 ml portion of 10N aqueous sodium hydroxide was added to 2.3 g of 4-[[4-[(3-bromophenyl)amino]-6-quinazolinyl]amino]-4oxo-(E)-2-butenoic acid ethyl ester (Example 5) in 25 ml of ethanol. After stirring for an hour, 2.1 ml of concentrated hydrochloric acid was added, and the reaction was stirred an additional 2 hours. The resulting solid was recrystallized from n-butanol to give 0.97 g of 4-[[4-[(3-Bromophenyl)amino]-6-quinazolinyl]amino]-4-oxo-(E)-2-butenoic acid: mass spectrum (m/e): M+H 413.

EXAMPLE 11

N-[4-[(3-Bromophenyl)amino]-6-quinazolinyl]-2,4-hexadienamide

A solution of 0.67 g of 2,4-hexadienoic acid in 10 ml of tetrahydrofuran was cooled in an ice bath. A 0.79 ml portion of isobutyl chloroformate followed by a 0.66 ml portion of N-methyl morpholine were added. After about 1 minute a solution of 1.6 g of N-(3-bromophenyl)-4,6-quinazolindiamine in 10 ml of pyridine was added. The reaction was allowed to come to room temperature and stir overnight. The solvents were removed at reduced pressure and the solid was recrystallized to give 1.0 g of N-[4-[(3-bromophenyl)amino]-6-quinazolinyl]-2,4-hexadienamide: mp=258°–260° C.

EXAMPLE 12

N-[4-[(3-Bromophenyl)amino]-6-quinazolinyl]-2-cyclopenteneamide

A solution of 0.43 g of 2-cyclopentenoic acid in 5 ml of tetrahydrofuran was cooled in an ice bath. A 0.49 ml portion of isobutyl chloroformate followed by a 0.41 ml portion of N-methyl morpholine were added. After about 1 minute a solution of 1.0 g of N-(3-bromophenyl)-4,6-quinazolindiamine in 10 ml of pyridine was added. The reaction was allowed to come to room temperature and stir overnight. Another 0.5 equivalents of mixed anhydride was added. The mixture was stirred for 5 hours. The solvents were removed at reduced pressure and the solid was purified by chromatography on silica gel to give 0.30 g of N-[4-[(3-bromophenyl)amino]-6-quinazolinyl]-2-cyclopenteneamide: mass spectrum (m/e): 409 (M+H, EI).

EXAMPLE 13

N-[4-[(3-Bromophenyl)amino]-6-quinazolinyl]-2-propenamide

A solution of 2.0 g of N-(3-bromophenyl)-4,6-quinazolindiamine in 10 ml of pyridine was cooled in an ice bath and a solution of 0.61 ml of acryoyl chloride in 30 ml of ether was added dropwise at 0° C. After stirring at room temperature for 3.5 hours, the solvents were removed at reduced pressure. The residue was purified by chromatography to give 0.2 g of N-[4-[(3-bromophenyl)amino]-6-quinazolinyl]-2-propenamide: mass spectrum (m/e): M+H 369.

EXAMPLE 14

N-[4[(3-Bromophenyl)amino]-6-quinazolinyl]-(3-phenyl-2-propynamide)

A solution of 0.93 g of 3-phenyl-2-propynoic acid in 10 ml of tetrahydrofuran was cooled in an ice bath. A 0.82 ml portion of isobutyl chloroformate followed by a 0.69 ml portion of N-methyl morpholine were added. After about 1 minute a solution of 1.0 g of N-(3-bromophenyl)-4,6-quinazolindiamine in 7 ml of pyridine was added. The reaction at 0° C. for 1 hr. The solvents were removed at reduced pressure and the solid was purified by chromatography on silica gel to give 0.01 g of N-[4-[(3-bromophenyl)amino]-6-quinazolinyl]-(3-phenyl-2-propynamide): mass spectrum (m/e): 443.2, 445.2 (M+H, electrospray).

EXAMPLE 15

6-amino-4-chloroquinazoline

A mixture consisting of 3.25 g of 4-chloro-6-nitroquinazoline, 10.8 g of sodium hydrosulfite, and 0.3 g of the phase transfer catalyst $(C_8H_{17})_3NCH_3+Cl^-$ in 97 ml of tetrahydrofuran and 32 ml of water was stirred rapidly for 2 hours. The mixture was diluted with ether and the organic layer was separated. The organic solution was washed with brine and then dried over magnesium sulfate. The solution was passed through a small column of silica gel. The solvent was removed at 30° C. at reduced pressure giving 6-amino-4-chloroquinazoline which is used in the next step without additional purification.

EXAMPLE 16

[4-chloro-6-quinazolinyl]-2-butynamide

A solution of 1.64 g of 2-butynoic acid in 46 ml of tetrahydrofuran was cooled in an ice bath. A 2.34 ml portion of isobutyl chloroformate followed by a 4.13 ml portion of N-methyl morpholine were added. After about 10 minutes, this was poured into a solution of 6-amino-4-chloroquinazoline in 46 ml tetrahydrofuran. This mixture was stirred at room temperature for 2 hours. The mixture was poured into a mixture of brine and saturated sodium bicarbonate and extracted with ether. The ether solution was dried over magnesium sulfate and filtered. The solvent was removed giving [4chloro-6-quinazolinyl]-2-butynamide as colored oil that was used in the next step without additional purification.

EXAMPLE 17

N-[4-[(3-Bromophenyl)amino]-6-quinazolinyl]-2-butynamide

A solution consisting of 1.76 g of [4chloro-6-quinazolinyl]-2-butynamide and 1.23 g of 3-bromo aniline was refluxed under an inert atmosphere in 23 ml of isopropanol for 40 minutes. The mixture was cooled to room temperature and 200 ml of ether was added giving 0.4 g of N-[4-[(3-bromophenyl)amino]-6-quinazolinyl]-2-butynamide as the hydrochloride salt. Neutralizing with sodium bicarbonate solution, extracting with ethyl acetate, removal of the solvent, and recrystallization from 1-butanol gives N-[4-[(3-bromophenyl)amino]-6-quinazolinyl]-2-butynamide as the free base.

EXAMPLE 18

N'-(4-Amino-2-cyanophenyl)-N,N-dimethylformamidine

A solution of 6.0 g (27.5 mmol) of N'-(2-cyano-4-nitrophenyl)-N,N-dimethylformamidine, 33.9 g (41.8 ml, 412.4 mmol) of cyclohexene, and 0.6 g of 10% Pd/C in 360 ml of methanol was refluxed for 4 hrs. The hot mixture was filtered through Celite. Solvent was removed and the residue was recrystallized from chloroform-carbon tetrachloride giving 4.9 g (95%) of the title compound as a light gray crystalline solid. mass spectrum (m/e):188.9 (M+H, electrospray).

EXAMPLE 19

N-[3-Cyano-4-[[(dimethylamino)methylene]amino]phenyl]-2-butynamide

To a solution of 2.01 g (23.9 mmol) of 2-butynoic acid and 2.9 ml (22.3 mmol) isobutyl chloroformate in 30 ml tetrahydrofuran was stirred at 0° C. under nitrogen as 2.42 g (2.63 ml, 22.3 mmol) of N-methyl morpholine was added over 3 min. After stirring for 15 min., a solution of N'-(4-amino-2-cyanophenyl)-N,N-dimethylformamidine and 1.6 g (1.75 ml, 15.9 mmol) of N-methyl morpholine in 25 ml tetrahydrofuran was added over 4 min. The mixture was stirred 30 min. at 0° C. and 30 min. at room temperature. The mixture was diluted with 70 ml of ethyl acetate and poured into a mixture of brine and saturated sodium bicarbonate. The organic layer was dried (MgSO$_4$) and filtered through a pad of silica gel. The solvent was removed and the residue was stirred with 50 ml of ether. The suspended solid was collected to give 3.61 g (89%) of an off-white solid. mass spectrum (m/e): 255.0 (M+H, electrospray).

EXAMPLE 20

N-[4-[(3-Bromophenyl)amino]-6-quinazolinyl]-2-butynamide

A solution of 3.0 g (11.8 mmol) of N-[3-cyano-4-[[(dimethylamino)methylene]amino]phenyl]-2-butynamide and 2.23 g (12.98 mmol) of 3-bromo aniline in 18 ml of acetic acid was refluxed gently with stirring under nitrogen for 1 hr 15 min. The mixture was cooled in an ice bath and a solid mass formed. The solid was collected by filtration and washed with ether-acetonitrile 1:1 to give a yellow solid which was recrystallized from ethanol giving 2.51 g of N-[4-[(3-bromophenyl)amino]-6-quinazolinyl]-2-butynamide: mass spectrum (m/e): 381, 383.

We claim:

1. A compound of the formula

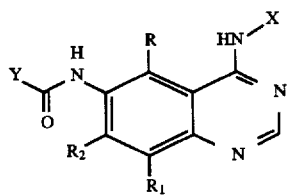

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and R$_1$ are each, independently, hydrogen, halogen, alkyl of 1–6 carbon atoms, alkoxy of 1–6 carbon atoms, hydroxy, or trifluoromethyl;

R$_2$ is hydrogen, alkyl of 1–6 carbon atoms, alkoxy of 1–6 carbon atoms, hydroxy, trifluoromethyl;

Y is a radical selected from the group consisting of

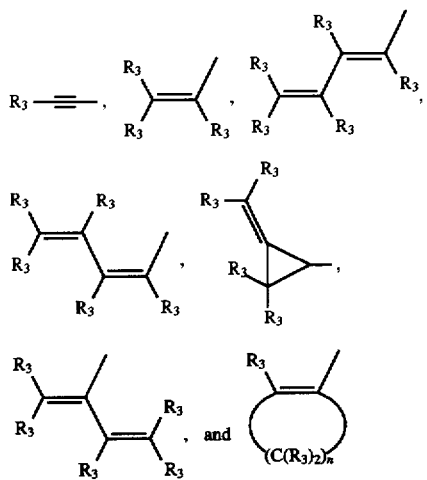

R$_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each R$_3$ of Y may be the same or different.

2. The compound according to claim 1 wherein R, R$_1$, and R$_2$ are hydrogen or a pharmaceutically acceptable salt thereof.

3. A compound according to claim 2 wherein X is unsubstituted or substituted with halogen or alkyl of 1–6 carbon atoms.

4. A compound according to claim 1 which is N-[4-[(3-Bromophenyl)amino]-6-quinazolinyl]-2-butynamide or a pharmaceutically acceptable salt thereof.

5. A compound according to claim 1 which is N-[4-[(3-Bromophenyl)amino]-6-quinazolinyl]-2-methyl-2-propenamide or a pharmaceutically acceptable salt thereof.

6. A compound according to claim 1 which is N-[4-[(3-Bromophenyl)amino]-6-quinazolinyl]-2,4-hexadienamide or a pharmaceutically acceptable salt thereof.

7. A compound according to claim 1 which is N-[4-[(3-Bromophenyl)amino]-6-quinazolinyl]-(E)-2-butenamide or a pharmaceutically acceptable salt thereof.

8. A compound according to claim 1 which is N-[4-[(3-Bromophenyl)amino]-6-quinazolinyl]-3-methyl-2-butenamide or a pharmaceutically acceptable salt thereof.

9. A compound according to claim 1 which is 4-[[4-[(3-Bromophenyl)amino]-6-quinazolinyl]amino]-4-oxo-(Z)-2-butenoic acid or a pharmaceutically acceptable salt thereof.

10. A compound according to claim 1 which is 4-[[4-[(3-Bromophenyl)amino]-6-quinazolinyl]amino]-4-oxo-(E)-2-butenoic acid or a pharmaceutically acceptable salt thereof.

11. A compound according to claim 1 which is 4-[[4-[(3-Bromophenyl)amino]-6-quinazolinyl]amino]-4-oxo-(E)-2-butenoic acid, ethyl ester or a pharmaceutically acceptable salt thereof.

12. A compound according to claim 1 which is N-[4-[(3-bromophenyl)amino]-6-quinazolinyl]-2-cyclopentenamide or a pharmaceutically acceptable salt thereof.

13. A compound according to claim 1 which is N-[4-[(3-Bromophenyl)amino]-6-quinazolinyl]-2-propenamide or a pharmaceutically acceptable salt thereof.

14. A compound according to claim 1 which is N-[4-[(3-bromophenyl)amino]-6-quinazolinyl]-(3-phenyl-2-propynamide) or a pharmaceutically acceptable salt thereof.

15. A method of inhibiting the biological effects of a deregulated protein tyrosine kinase in a mammal which comprises administering to said mammal an effective amount of a compound having the formula

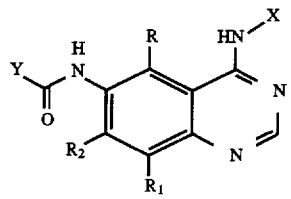

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

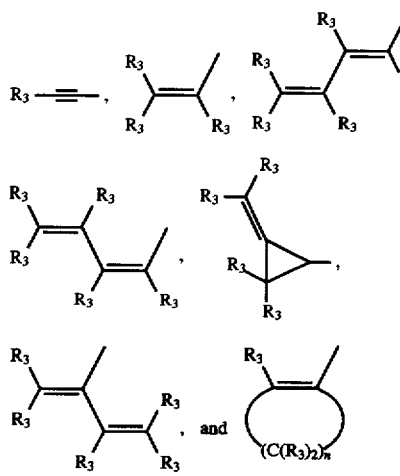

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different.

16. A method of treating, inhibiting the growth of, or eradicating neoplasms in a mammal which comprises administering to said mammal an effective amount of a compound having the formula

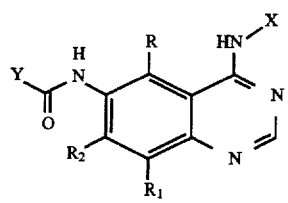

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

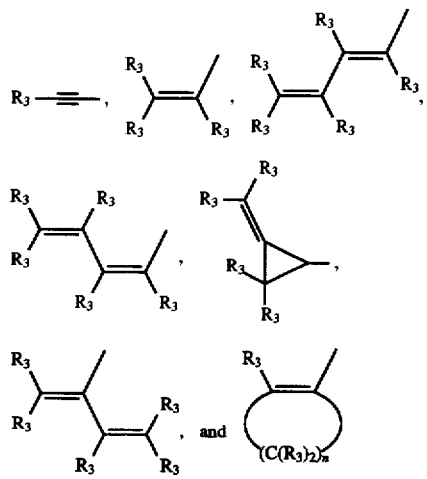

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different.

17. The method according to claim 15 wherein the neoplasm expresses EGFR.

18. The method according to claim 16 wherein the neoplasm is selected from the group consisting of breast, kidney, bladder, mouth, larynx, esophagus, stomach, colon, ovary, and lung.

19. A pharmaceutical composition which comprises a compound having the formula

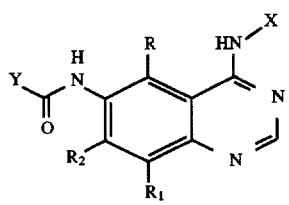

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

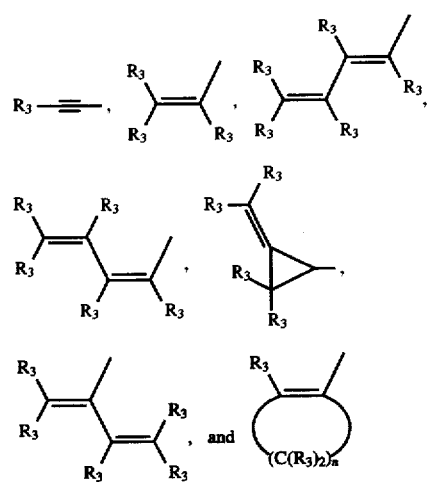

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different and a pharmaceutically acceptable carrier.

20. A process for producing a compound of the formula:

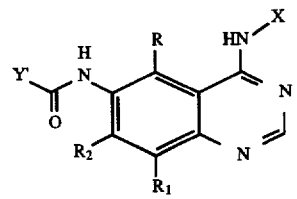

wherein R, $R_1$, $R_2$, and X, are as according to claim 1; Y' is a radical selected from the group consisting of:

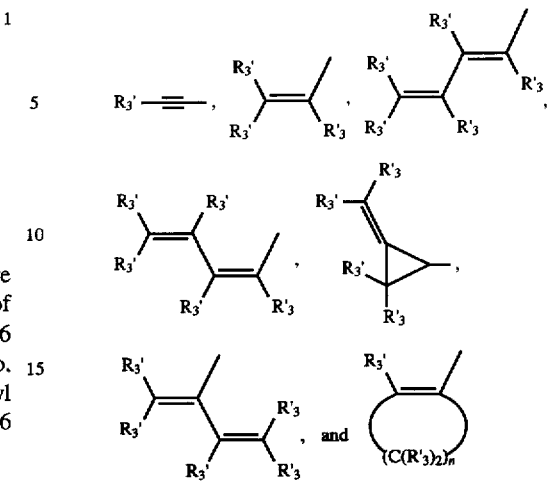

wherein each $R'_3$ is independently hydrogen, alkyl of 1–6 carbon atoms, carboxy, carboalkoxy of 1–6 carbon atoms, phenyl, or carboalkyl of 2–7 carbon atoms; n is the integer 2–4, which comprises treating an anthranilonitrile of the formula:

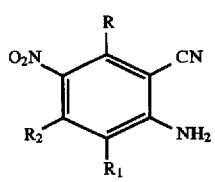

with dimethylformamide dimethyl acetal with or without solvent to give a compound of the formula:

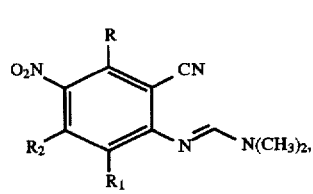

heating said compound with an aniline of the formula:

in an acidic organic solvent to give a 6-nitro-quinazoline of the formula:

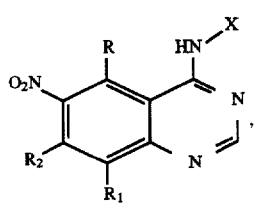

treating said compound with a reducing agent to give a 6-amino-quinazoline of the formula:

[structure: H2N-substituted aryl with R, R1, R2, and HN-X, C=N, N group], and reacting said compound with an acid chloride or mixed anhydride of the formulas:

Y'—C(=O)—Cl  and  Y'—C(=O)—OCOR4 wherein $R_4$ is alkyl of 1–6 carbon atoms.

21. A process for producing a compound of the formula:

[structure showing HO2C-C(R5)=C(R5)-C(=O)-NH- aryl with R, R1, R2, HN-X, C=N, N]

wherein R, $R_1$, $R_2$, and X, are as according to claim 1 and (Z) indicates the configuration of the double bond which comprises reacting compounds of the formula:

[structure: H2N-aryl(R,R1,R2)-C(=NX)H-N=CH-N]

with a cyclic anhydride of the formula:

[cyclic anhydride with R5, R5 substituents]

wherein each $R_5$ is independently hydrogen, phenyl, or alkyl of 1–6 carbon atoms in an inert solvent in the presence of an organic base.

22. A process for producing a compound of the formula:

[Y'-C(=O)-NH-aryl-C(=NX)-N=CH-N structure]

wherein X and Y' are as according to claim 20, which comprises reducing a compound of the formula:

[O2N-aryl-C(Cl)=N-aryl-N=CH-N structure]

with sodium hydrosulfite and a phase transfer catalyst in a solvent mixture comprising an inert organic solvent and water to give a compound of the formula:

[H2N-aryl-C(Cl)=N-...-N=CH-N structure], reacting said compound with an acid chloride or mixed anhydride of the formula:

Y'—C(=O)—Cl  or  Y'—C(=O)—OCOR4 wherein $R_4$ is alkyl of 1–6 carbon atoms, in the presence of an amine base in an inert solvent to give a compound of the formula:

[Y'-C(=O)-NH-aryl-C(Cl)=N-...-N=CH-N structure], and heating said compound with an aniline of the formula:

X—NH2 in an inert solvent.

23. A process for producing a compound of the formula:

[Y'-C(=O)-NH-aryl-C(=NX)-N=CH-N structure]

wherein X and Y' are as according to claim 20, which comprises reducing the compound of the formula:

[O2N-aryl-CN with N=CH-N(CH3)2 substituent]

with a palladium catalyst and a source of hydrogen in an inert solvent to give a compound of the formula:

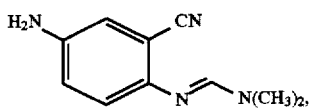
reacting said compound with an acid chloride or mixed anhydride of the formula:
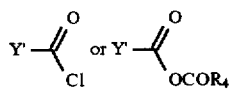
wherein $R_4$ is alkyl of 1–6 carbon atoms, in the presence of an amine base in an inert solvent to give a compound of the formula:
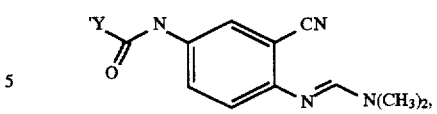
and heating said compound with an aniline of the formula:
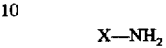
in an acidic solvent.
* * * * *